US009987623B2

(12) United States Patent
Domokos et al.

(10) Patent No.: US 9,987,623 B2
(45) Date of Patent: Jun. 5, 2018

(54) PROCESS FOR THE PREPARATION OF A CATALYST SUPPORT

(71) Applicant: SHELL OIL COMPANY, Houston, TX (US)

(72) Inventors: László Domokos, Amsterdam (NL); Peter Geerinck, Wondelgem (BE); Aan Hendrik Klazinga, Voorschoten (NL)

(73) Assignee: SHELL OIL COMPANY, Houston, TX (US)

( * ) Notice: Subject to any disclaimer, the term of this patent is extended or adjusted under 35 U.S.C. 154(b) by 0 days. days.

(21) Appl. No.: 15/838,439

(22) Filed: Dec. 12, 2017

(65) Prior Publication Data
US 2018/0099266 A1 Apr. 12, 2018

Related U.S. Application Data

(62) Division of application No. 15/431,962, filed on Feb. 14, 2017, now Pat. No. 9,873,111, which is a division of application No. 13/641,710, filed as application No. PCT/EP2011/056171 on Apr. 18, 2011, now Pat. No. 9,604,204.

(30) Foreign Application Priority Data

Apr. 19, 2010 (EP) ..................... 10160259

(51) Int. Cl.
B01J 29/06 (2006.01)
C07C 4/18 (2006.01)
B01J 29/44 (2006.01)
B01J 37/00 (2006.01)
B01J 37/02 (2006.01)
B01J 29/40 (2006.01)
B01J 37/08 (2006.01)
B01J 35/02 (2006.01)
B01J 37/04 (2006.01)
B01J 35/10 (2006.01)
B01J 37/30 (2006.01)
B01J 35/00 (2006.01)
C07C 15/04 (2006.01)

(52) U.S. Cl.
CPC ............ B01J 29/44 (2013.01); B01J 29/405 (2013.01); B01J 35/0006 (2013.01); B01J 35/023 (2013.01); B01J 35/10 (2013.01); B01J 35/1019 (2013.01); B01J 35/1042 (2013.01); B01J 37/0009 (2013.01); B01J 37/0207 (2013.01); B01J 37/04 (2013.01); B01J 37/08 (2013.01); B01J 37/30 (2013.01); C07C 4/18 (2013.01); C07C 15/04 (2013.01); B01J 2229/16 (2013.01); B01J 2229/186 (2013.01); B01J 2229/20 (2013.01); B01J 2229/32 (2013.01); B01J 2229/42 (2013.01); C07C 2529/40 (2013.01); C07C 2529/44 (2013.01)

(58) Field of Classification Search
CPC ...... B01J 29/44; B01J 29/405; B01J 2229/42; B01J 2229/20; B01J 2229/32; B01J 2229/186; B01J 2229/16; B01J 35/023; B01J 35/1019; B01J 35/1042; B01J 35/0006; B01J 37/0009; B01J 37/04; B01J 37/0207; B01J 37/08; B01J 37/30; C07C 2529/44; C07C 2529/40; C07C 4/18; C07C 15/04
USPC ............ 502/64, 69, 70, 71, 74, 77; 585/486, 585/488, 489
See application file for complete search history.

(56) References Cited

U.S. PATENT DOCUMENTS

| 3,929,672 | A | * | 12/1975 | Ward | B01J 20/18 423/713 |
|---|---|---|---|---|---|
| 5,516,956 | A | * | 5/1996 | Abichandani | B01J 29/44 585/475 |
| 6,709,570 | B1 | * | 3/2004 | Van Crijnen-Beers | B01J 29/06 208/109 |
| 2001/0051754 | A1 | * | 12/2001 | Lissy | B01J 29/40 585/319 |
| 2004/0082461 | A1 | * | 4/2004 | Remans | B01J 29/44 502/66 |

FOREIGN PATENT DOCUMENTS

EP 2 027 917 * 2/2009

* cited by examiner

Primary Examiner — Elizabeth D Wood
(74) Attorney, Agent, or Firm — Charles W. Stewart

(57) ABSTRACT

Process for preparing a catalyst support which process comprises a) mixing pentasil zeolite having a bulk silica to alumina molar ratio in the range of from 20 to 150 with water, a silica source and an alkali metal salt, b) extruding the mixture obtained in step (a), c) drying and calcining the extrudates obtained in step (b), d) subjecting the calcined extrudates obtained in step (c) to ion exchange to reduce the alkali metal content, and e) drying the extrudates obtained in step (d); process for preparing a catalyst by furthermore impregnating such support with platinum in an amount in the range of from 0.001 to 0.1 wt % and tin in an amount in the range of from 0.01 to 0.5 wt %, each on the basis of total catalyst; ethylbenzene dealkylation catalyst obtainable thereby and a process for dealkylation of ethylbenzene which process comprises contacting feedstock containing ethylbenzene with such catalyst.

18 Claims, No Drawings

PROCESS FOR THE PREPARATION OF A CATALYST SUPPORT

This Application is a divisional of U.S. application Ser. No. 15/431,962, filed Feb. 14, 2017, now U.S. Pat. No. 9,873,111 which is a divisional of U.S. application Ser. No. 13/641,710, filed Oct. 17, 2012, now U.S. Pat. No. 9,604,204, issued Mar. 28, 2017, which is a National Stage (§ 371), entry of International Application No. PCT/EP2011/056171, filed Apr. 18, 2011, which claims priority to European Application No. 10160259.7, filed Apr. 19, 2010, the disclosures of which are incorporated herein by reference.

The present invention relates to a process for the preparation of a catalyst support and a catalyst, ethylbenzene dealkylation catalyst obtainable thereby and process using such catalyst.

BACKGROUND OF THE INVENTION

Ethylbenzene is one of the aromatic hydrocarbons that is obtained from naphtha pyrolysis or in reformate. Reformate is an aromatic product given by the catalysed conversion of straight-run hydrocarbons boiling in the 70 to 190° C. range, such as straight-run naphtha. Such hydrocarbons are themselves obtained by fractionation or distillation of crude petroleum oil, their composition varying depending on the source of the crude oil, but generally having a low aromatics content. On conversion to reformate, the aromatics content is considerably increased and the resulting hydrocarbon mixture becomes highly desirable as a source of valuable chemicals intermediates and as a component for gasoline. The principle components are a group of aromatics often referred to as BTX: benzene, toluene, and the xylenes, including ethylbenzene. Other components may be present such as their hydrogenated homologues, e.g. cyclohexane.

Of the BTX group the most valuable components are benzene and the xylenes, and therefore BTX is often subjected to processing to increase the proportion of those two aromatics: hydrodealkylation of toluene to benzene and toluene disproportionation to benzene and xylenes. Within the xylenes, para-xylene is the most useful commodity and xylene isomerisation or transalkylation processes have been developed to increase the proportion of para-xylene.

A further process that the gasoline producer can utilize is the hydrodealkylation of ethylbenzene to benzene.

Generally, the gasoline producer will isolate BTX from the reformate stream, and then subject the BTX stream to xylene isomerisation with the aim of maximising the para-xylene component. Xylene isomerisation is a catalytic process; some catalysts used in this process have the ability not just to isomerise xylenes but also simultaneously to dealkylate the ethylbenzene component. Normally the para-xylene is then separated out to leave benzene, toluene (unless toluene conversion processes have already been applied) and the remaining mixed xylenes, including ethylbenzene. This BTX stream can either be converted by transalkylation to increase the yield of xylenes by contacting with a heavier hydrocarbon stream or can be converted by dealkylation to eliminate selectively ethylbenzene and to increase the yield of benzene, while allowing the xylenes to reach equilibrium concentrations. The latter process is the subject of the present invention.

In ethylbenzene dealkylation at this latter stage of BTX treatment, it can be desirable to have a catalyst with high activity. Such catalyst makes it possible to operate at high weight hourly space velocities. Additionally, it is advantageous if a catalyst has high flat plate crushing strength as this leads to less fines and broken material being formed during handling and catalyst loading or unloading from the reactor. Fines are known to cause problems in operation such as contributing significantly to the pressure drop over a reactor.

Ethylbenzene dealkylation catalysts are well known in the art and typically comprise platinum on a zeolite containing support as described for example in EPA0018498.

WO2009016143 relates to ethylbenzene dealkylation catalysts comprising pentasil zeolite having a bulk silica to alumina ratio in the range of from 20 to 150, platinum and tin.

U.S. Pat. No. 4,582,815 describes a method for preparing silica-rich solids which comprises mixing silica-rich solids with water in an alkali metal base or basic salt followed by mulling, extruding, drying and neutralizing the base before calcination. Calcining can cause the alkali metal to become trapped, perhaps by encapsulation, and it is then difficult to remove by ion exchange and is usually removed incompletely. The products are described to be suitable for a wide variety of processes which are both non-catalytic and catalytic such as hydrocracking, isomerization, hydrogenation, dehydrogenation, polymerization, reforming, catalytic cracking and catalytic hydrocracking.

SUMMARY OF THE INVENTION

The present invention provides a process for preparing a catalyst support which process comprises:
a) mixing pentasil zeolite having a bulk silica to alumina molar ratio in the range of from 20 to 150 with water, a silica source and an alkali metal salt,
b) extruding the mixture obtained in step (a),
c) drying and calcining the extrudates obtained in step b),
d) subjecting the calcined extrudates obtained in step (c) to ion exchange to reduce the alkali metal content, and
e) drying the extrudates obtained in step (d).

Also provided is a process for preparing a catalyst on the basis of such support, an ethylbenzene dealkylation catalyst obtainable thereby and a process for dealkylation of ethylbenzene which process comprises contacting feedstock containing ethylbenzene, preferably feedstock containing $C_7$ to $C_9$ aromatics, including xylenes and ethylbenzene, with a catalyst of the present invention.

DETAILED DESCRIPTION OF THE INVENTION

Support according to the present invention has been found to give a catalyst having increased activity. An additional advantage of the present invention is that it was found possible to prepare catalysts having a high flat plate crushing strength.

Silica is preferably used as a binder in the present invention and may be a naturally occurring silica or may be in the form of a gelatinous precipitate, sol or gel. The form of silica is not limited and the silica may be in any of its various forms: crystalline silica, vitreous silica or amorphous silica. The term amorphous silica encompasses the wet process types, including precipitated silicas and silica gels, or pyrogenic or fumed silicas. Silica sols or colloidal silicas are non-settling dispersions of amorphous silicas in a liquid, usually water, typically stabilized by anions, cations, or non-ionic materials.

The silica binder preferably is a mixture of two silica types, most preferably a mixture of a powder form silica and a silica sol. Conveniently powder form silica has a B.E.T. surface area in the range of from 50 to 1000 $m^2/g$; and a mean particle size in the range of from 2 nm to 200 µm, preferably in the range of from 2 to 100 µm, more preferably 2 to 60 µm, especially 2 to 10 µm as measured by ASTM C 690-1992 or ISO 8130-1. A very suitable powder form silica material is Sipernat 50, a white silica powder having predominantly spherical particles, available from Degussa (Sipernat is a trade name) A very suitable silica sol is that sold under the trade name of Bindzil by Eka Chemicals. Where the mixture comprises a powder form silica and a silica sol, then the two components may be present in a weight ratio of powder form to sol form in the range of from 1:1 to 10:1, preferably 2:1 to 5:1, more preferably from 2:1 to 3:1. The binder may also consist essentially of just the powder form silica.

Where a powder form of silica is used as a binder in the catalyst composition of the present invention, preferably a small particulate form is utilized, which has a mean particle size in the range of from 2 to 10 µm as measured by ASTM C 690-1992. An additional improvement in support strength is found with such materials. A very suitable small particulate form is that available from Degussa under the trade name Sipernat 500LS.

Preferably the silica component is used as a pure silica and not as a component in another inorganic oxide. It is most preferred that the silica and indeed the support, is essentially free of any other inorganic oxide binder material, and especially is free of alumina. At most only a maximum of 2 wt % alumina, based on the total support, is present.

In preferred embodiments which utilize a surface modification dealumination treatment, the presence of alumina can particularly be detrimental since with an alumina support the surface modification would detrimentally affect the physical integrity of the support.

Pentasil zeolites are well known to the skilled person. 'Pentasil' is a term used to describe a class of shape-selective zeolites which are typically characterized by a silica to alumina ratio (SAR) of at least 12 and are constructed of five-membered rings (their framework being built up from 5-1 secondary building units). The pentasil zeolite utilized in the present invention has a SAR in the range of from 20 to 150. The SAR is the bulk or overall silica/alumina ratio which may or may not be different to the framework SAR depending on any treatment to which the zeolite, either when free or in catalyst form, has been subjected.

Of the pentasil zeolites, the preferred zeolites are ZSM-5, ZSM-8, ZSM-11, ZSM-12, TON, e.g. ZSM-22, ZSM-23, ZSM-35, e.g. ferrierite, and ZSM-48, with those having the MFI configuration, and especially ZSM-5, being the most preferred. All of these zeolites are well known and documented in the literature; see for example the Database of Zeolite Structures: http://www.iza-structure.org/databases/ or Baerlocher et al., "Atlas of Zeolite Framework Types", 5$^{th}$ Rev. Ed. (2001), published on behalf of the Structure Commission of the International Zeolite Association, by Elsevier. Pentasil zeolites are reviewed in the Database at http://www.iza-structure.org/databases/Catalog/Pentasils.pdf.

Such zeolites can exist in various forms depending on the ion present at the cation sites in the zeolite structure. Generally the available forms contain an alkali metal ion, an alkaline earth metal ion, or a hydrogen or hydrogen precursor ion at the cation site. In the catalyst composition of the present invention, the zeolite is present in the form containing hydrogen or hydrogen precursor; this form is commonly known as the H$^+$ form. The zeolite may be used either in its template-free or its template-containing form. Some advantage in reduction of xylene loss has been found where the template-containing form is used during the preparation.

The SAR of such zeolites is preferably at least 25, most preferably at least 30, and is preferably at most 100, most preferably at most 90, especially at most 50.

The zeolite starting material can exist in a number of particle size ranges. Suitably the zeolite has a primary particle diameter in the range of from 20 nm to 10 µm. Useful catalysts have been prepared using a large crystal size ZSM-5 zeolite having an average crystallite size in the range of from 1 to 10 µm and also using a small particle size ZSM-5 having a primary particle diameter below 200 nm. Generally, in terms of particle size distributions, the ZSM-5 may have a particle size distribution in which the diameter of 50% of the particles, D(v, 0.5), is greater than 2 µm and that of 90% of the particles, D(v, 0.9), is less than 30 µm.

Suitable ZSM-5 materials can be prepared by procedures documented in the literature, for example in U.S. Pat. No. 3,702,886, in references provided in the Atlas, or Database of Zeolite Structures, and in other literature references such as by Yu et al in Microporous and Mesoporous Materials 95 (2006) 234 to 240, and Iwayama et al in U.S. Pat. No. 4,511,547.

Suitable grades of ZSM-5 zeolite include CBV 3014E, CBV 8014, and CBV 3020E, available commercially from Zeolyst International.

The zeolite is an important factor in the activity and selectivity properties shown by the catalyst composition of the invention. There is a balance between the activity and selectivity desired which may result in a different optimum zeolite content in the support depending on the zeolite used and the SAR of the zeolite used. Generally a higher zeolite content may in some cases be advantageous to produce a higher activity from the catalyst composition, while a lower zeolite content may provide a higher selectivity. If a higher SAR zeolite is used, the proportion of zeolite in the catalyst support tends to have to be increased to achieve optimum performance.

While the balance between SAR and zeolite content may cause a different optimum depending on the conditions utilized in the ethylbenzene dealkylation process, generally it is preferred to minimize the amount of zeolite used in the catalyst support, since a higher amount of zeolite may negatively affect the physical properties of the catalyst support such as lowering its strength. It is generally preferred that the support is composed of in the range of from 30 to 80 wt %, most preferably from 50 to 70 wt %, silica and in the range of from 20 to 70 wt %, most preferably from 30 to 50 wt %, zeolite.

A very suitable catalyst support for the present invention contains a pentasil zeolite, especially ZSM-5, having a SAR in the range of from 20 to 50, especially 30 to 40, in an amount in the range of from 20 to 50 wt %, especially 25 to 40 wt %.

The alkali metal salt can be chosen from a large variety of compounds. The alkali metal preferably is sodium or potassium, more preferably sodium. Furthermore, it is preferred that the compound is basic, i.e. a 1 N aqueous solution of the salt has a pH of more than 8 at room temperature. More specifically, it is preferred that a 1 N aqueous solution of the salt has a pH of more than 9, preferably at least 10, more preferably at least 11. The alkali metal salt preferably is selected from the group consisting of sodium hydroxide, potassium hydroxide and sodium silicate. Most preferably, the alkali metal salt is sodium hydroxide and/or waterglass.

Preferably there is no other component than binder, preferably silica, pentasil zeolite and alkali metal salt in the mixture of step (a). However it is possible to include up to 10 wt % of other components whilst still obtaining the benefits of the present invention. Such other components may be selected from other refractory inorganic oxide binder materials and other zeolites. Other binder materials may be alumina, and magnesia. Examples of other zeolites are 8, 10, or 12-membered ring zeolites, for example mordenite, and zeolite beta, and acidic mesoporous materials such as the MCM-series of zeolites, e.g. MCM-22 and MCM-41.

Preferably, no further water is added to the extrusion mixture. The amount of water is preferably of from 40 to 65% by weight (% wt), based on dry mixture, more preferably of from to 45 to 60% wt.

Modification of the pentasil zeolite reduces the mole percentage of alumina which basically implies that the number of acid sites is reduced. This can be achieved in various ways. A first way is applying a coating of a low acidity inorganic refractory oxide onto the surface of the crystallites of the zeolite. Suitable inorganic oxides for this purpose are silica, zirconia or titania, of which silica is preferred. By applying such coating onto the crystallites' surface, the total number of oxide moieties in the modified zeolite (i.e. the original zeolite plus the coating) is increased, whilst the number of alumina moieties remains the same, thus resulting in a reduced mole percentage of alumina. A major advantage of this method is that the number of acid sites on the surface of the crystallites of the zeolite is drastically reduced to essentially nil.

Another very useful way of modifying the pentasil zeolite is by subjecting it to a dealumination treatment. In general, dealumination of the crystallites of a molecular sieve refers to a treatment, whereby aluminium atoms are either withdrawn from the zeolite framework leaving a defect or are withdrawn and replaced by other atoms, such as silicon, titanium, boron, germanium or zirconium. Dealumination can be attained by methods known in the art. Particularly useful methods are those, wherein the dealumination selectively occurs, or is claimed to occur selectively, at the surface of the crystallites of the zeolite. In this way, namely, the same effect as with the coated zeolites can be attained: the number of acid sites at the surface of the crystallites is reduced.

Another method for dealuminating the surface of zeolite crystallites is disclosed in U.S. Pat. No. 5,242,676. According to this method a zeolite is contacted with a dicarboxylic acid, suitably in the form of an aqueous solution, for sufficient time to effect at least 40% reduction in surface acidity with less than 50% overall dealumination. A very suitable dicarboxylic acid is oxalic acid, whilst suitable zeolites should have a Constraint Index of greater than 1 and include ZSM-5, ZSM-11, ZSM-23, and ZSM-35.

Yet another method for obtaining a zeolite having a dealuminated outer surface is disclosed in U.S. Pat. No. 4,088,605. According to this "in situ dealumination" method a zeolite having an aluminium-free outer shell of silica is produced by a two stage method comprising (i) initiating crystallization in a crystallization medium to form the zeolite and (ii) altering the crystallization medium to substantially eliminate the aluminium therein, suitably by adding a complexing agent to the crystallization mixture which forms a complex with the aluminium ions present, after which the complex formed is removed. Examples of suitable complexing agents are gluconic acid, tartaric acid and ethylenediamine-tetraacetic acid (EDTA). Zeolites having an aluminium-free outer shell which can be produced in this manner include ZSM-5 and ZSM-35.

It has been found especially advantageous to treat the extrudates obtained in step (c) with an aqueous solution of a fluorosilicate salt wherein the fluorosilicate salt is represented by the formula:

$$(A)_{2/b}SiF_6$$

wherein 'A' is a metallic or non-metallic cation other than H+ having the valence 'b'. Examples of cations 'b' are alkylammonium, $NH_4^+$, $Mg^{++}$, $Li^+$, $Na^+$, $K^+$, $Ba^{++}$, $Cd^{++}$, $Cu^+$, $Ca^{++}$, $Cs^+$, $Fe^{++}$, $Co^{++}$, $Pb^{++}$, $Mn^{++}$, $Rb^+$, $Ag^+$, $Sr^{++}$, $Tl^+$, and $Zn^{++}$. Preferably 'A' is the ammonium cation. The molecular sieve or molecular sieve-binder extrudate material may be contacted with the fluorosilicate salt in an amount of at least 0.0075 moles per 100 grams of the molecular sieve or molecular sieve-binder extrudate material. The pH is suitably between 3 and 7. Such treatment has been described in U.S. Pat. No. 6,949,181. It is thought that in this way aluminium atoms located at the surface of the zeolite are extracted and replaced with silicon atoms.

The dealumination of the aluminosilicate zeolite results in a reduction of the number of alumina moieties present in the zeolite and hence in a reduction of the mole percentage of alumina.

Of the (surface) dealumination methods described above, the method involving the treatment with a hexafluorosilicate, most suitably ammoniumhexa-fluorosilicate (AHS), has been found to offer an additional advantage. Treatment of the extrudates obtained in step c) with AHS, has been found to result in the extrudates also having an increased mechanical strength in addition to the expected dealuminated outer surface.

The surface modification may be applied just once to the support or may be applied two or more times. However we have not found any advantage in repeated application. The concentration of the AHS treatment does however appear to have an effect. Preferably the concentration of active ingredient (AHS) is in the range of from 0.005 to 0.5 M. Preferably, the concentration is in the range of from 0.01 to 0.2 M, more preferably 0.01 to 0.05 M, and especially 0.01 to 0.03 M, which has been found to provide a catalyst composition having an increased activity.

In step (c), the extrudates are dried and calcined. Drying preferably is carried out for a time in the range of 15 minutes to 24 hours, more preferably from 1 to 3 hours, at a temperature in the range from 10 to 350° C., more preferably from 120 to 150° C. Calcination is carried out under normal conditions, suitably at a temperature of between 400 to 900° C. by heating in air for 1 to 48, preferably 1 to 10 hours.

The extrudates obtained in step (c) are subjected to ion exchange in order to reduce their alkali metal content. The presence of alkali metal has been found to lead to reduced catalytic activity for ethylbenzene dealkylation. Preferably, the alkali metal content is reduced to at most 0.2% wt, expressed as $Na_2O$ based on total dry weight, more preferably at most 0.1% wt, more preferably at most 0.04% wt, more preferably at most 0.020% wt, most preferably at most 0.01% wt.

Someone skilled in the art will know which ion exchange to apply in order to achieve the desired reduction in alkali metal content. A suitable method comprises treating the extrudates with an aqueous ammonium containing solution such as ammonium chloride. A suitable treatment comprises immersing the extrudates in an ammonium chloride solution at a temperature of from 80 to 100° C., preferably about 90° C., for of from 0.2 to 5 hours, more specifically of from 0.5 to 2 hours.

It has been found to be especially advantageous to subject the extrudates obtained in step (c) to treatment with a hexafluorosilicate and subsequently apply ion exchange. In this way, only a single washing needs to be carried out while the alkali metal content can be reduced to very low levels.

In step (e), the extrudates are dried preferably for a time in the range of 15 minutes to 24 hours, more preferably from 1 to 3 hours, at a temperature in the range from 10 to 350° C., more preferably from 100 to 180° C.

The extrudates obtained in step (e) have a B.E.T. surface area preferably falling in the range of from 150 to 250 m$^2$/g; and a pore volume, by mercury intrusion, preferably in the range of from 0.5 to 0.9 ml/g. The flat plate crush strength generally is at least 120 N·cm$^{-1}$, preferably at least 140 N·cm$^{-1}$, more preferably at least 150 N·cm$^{-1}$, and most preferably at least 160 N·cm$^{-1}$. The flat plate crushing strength generally will be at most 200 N·cm$^{-1}$.

The catalyst support of the present invention preferably is converted into an ethylbenzene dealkylation catalyst by depositing platinum and tin on the support. The platinum component preferably is present in an amount in the range of from 0.001 to 0.1 wt %, based on total catalyst, and the tin component preferably is present in an amount in the range of from 0.01 to 0.5 wt %, based on total catalyst. Most suitably the platinum component is present in an amount in the range of from 0.01 to 0.1, preferably 0.01 to 0.05, wt %. The tin component is most suitably present in an amount in the range of 0.1 to 0.5, preferably 0.2 to 0.5, wt %.

The catalyst composition of the invention has properties similar to that of the support in B.E.T. surface area, pore volume and flat plate crush strength.

The metals emplacement onto the support may be by methods usual in the art. The metals can be deposited onto the support materials prior to shaping, but it is preferred to deposit them onto a shaped support.

Pore volume impregnation of the metals from a metal salt solution is a very suitable method of metals emplacement onto a shaped support. The metal salt solutions may have a pH in the range of from 1 to 12. The platinum salts that may conveniently be used are chloroplatinic acid and ammonium stabilized platinum salts. Examples of suitable tin salts utilized are stannous (II) chloride, stannic (IV) chloride, stannous sulphate, and stannous acetate. The metals may be impregnated onto the shaped support either sequentially or simultaneously. Where simultaneous impregnation is utilized the metal salts used must be compatible and not hinder the deposition of the metals. It has been found useful to utilize a complexing or chelating agent in a combined platinum/tin salt solution to prevent unwanted metals precipitation. Examples of suitable complexing agents are EDTA (ethylenediamine tetraacetic acid), and derivatives thereof, HEDTA (N-(2-hydroxyethyl)ethylenediamine-N,N', N'-triacetic acid), EGTA (ethylene glycol-bis(2-aminoethylether)-N,N,N',N'-tetraacetic acid), DTPA (diethylene tridiamine pentaacetic acid), and NTA (nitrilotriacetic acid). Where EDTA is used, it is conveniently used in a molar ratio to tin of from 0.1 to 3, especially 1 to 2.

After metals impregnation, the catalyst composition is suitably dried, and calcined. Drying temperatures are suitably 50 to 200° C.; drying times are suitably from 0.5 to 5 hours. Calcination temperatures are very suitably in the range of from 200 to 800° C., preferably 300 to 600° C. For calcination of the support, a relatively short time period is required, for example 0.5 to 3 hours. For calcination of the catalyst composition, it may be necessary to employ controlled temperature ramping at a low rate of heating to ensure the optimum dispersion of the metals: such calcination may require from 5 to 20 hours.

Prior to use, it is necessary to ensure that the metals on the catalyst composition are in metallic (and not oxidic) form. Accordingly, it is useful to subject the composition to reducing conditions, which are, for example, heating in a reducing atmosphere, such as in hydrogen optionally diluted with an inert gas, or mixture of inert gases, such as nitrogen and carbon dioxide, at a temperature in the range of from 150 to 600° C. for from 0.5 to 5 hours.

The catalyst composition of the invention finds especial use in the selective dealkylation of ethylbenzene.

The ethylbenzene feedstock most suitably originates directly from a reforming unit or naphtha pyrolysis unit or is the effluent of a xylene isomerisation unit. Such feedstock usually comprises $C_7$ to $C_9$ hydrocarbons, and in particular one or more of o-xylene, m-xylene, p-xylene, toluene, and benzene in addition to ethylbenzene. Generally the amount of ethylbenzene in the feedstock is in the range of from 0.1 to 50 wt % and the total xylene content is typically at least 20 wt %. Typically the xylenes will not be in a thermodynamic equilibrium, and the content of p-xylene will accordingly be lower than that of the other isomers compared with thermodynamic equilibrium.

The feedstock is contacted with the catalyst composition in the presence of hydrogen. This may be carried out in a fixed bed system, a moving bed system, or a fluidized bed system. Such systems may be operated continuously or in batch fashion. Preference is given to continuous operation in a fixed bed system. The catalyst may be used in one reactor or in several separate reactors in series or operated in a swing system to ensure continuous operation during catalyst change-out.

The process is suitably carried out at a temperature in the range of from 300 to 500° C., a pressure in the range of from 0.1 to 50 bar (10 to 5,000 kPa), using a liquid hourly space velocity of in the range of from 0.5 to 20 h$^{-1}$. A partial pressure of hydrogen in the range of from 0.05 to 30 bar (5 to 3,000 kPa) is generally used. The feed to hydrogen molar ratio is in the range of from 0.5 to 100, generally from 1 to 10 mol/mol. The present invention will now be illustrated by the following Examples.

EXAMPLES

In the Examples and where mentioned elsewhere hereinabove, the following test methods are applicable:
Flat plate crush strength: ASTM D 6175.
Porosity: ASTM D 4284 with drying of the sample at 300° C. for 60 minutes prior to measurement, and using mercury intrusion.
Water pore volume: the sample is dried at 300° C. for 1 hour and then weighed; water is added until the pores are filled such that the sample particles are wet but still free flowing;
the sample is again weighed and the amount of water absorbed per unit mass is calculated from the two weights.
The sodium content is the amount of Na2O based on total dry weight.
In the Examples, the zeolites were used in the H$^+$ form and free of template material.

Example 1

Catalyst 1 (Not According to the Invention)
A support was prepared from a zeolite with a ZSM-5 structure having an average primary crystal size below 100 nm and a silica to alumina bulk molar ratio of 40. The zeolite powder was mixed with a low sodium grade silica (Sipernat 50 from Degussa), and an ammonium stabilized commercially available silica sol (sold under the trade name Bindzil by Eka Chemicals), and extruded using 1.5 wt % of ammonium hydroxide solution (containing 25 wt % ammonia) on dry basis to give a support comprised of 40 wt % zeolite, 40 wt % Sipernat 50 and 20 wt % silica sol on dry basis.

The green extrudates were dried at 120° C. and calcined at 625° C. for 1 hour to obtain extrudates having a water pore volume of 0.76 ml.g$^{-1}$ and a flat plate crushing strength of 108 N·m$^{-1}$.

These extrudates were treated with 0.02 M aqueous ammonium hexafluorosilicate (AHS) solution and subsequently washed several times with water. The washed extrudates were subsequently dried at 500° C. for 1 hour. The resulting catalyst support had a flat plate crushing strength of 124 N·cm$^{-1}$.

Subsequently, the catalyst support was pore volume impregnated with a Pt/Sn solution having a pH below 2; the solution was prepared from $H_2PtCl_6$ and $SnCl_2.2H_2O$. The concentration of both metals was such as to provide a final catalyst having a Pt loading of 0.025 wt % and a Sn loading of 4% wt, each based on total catalyst. Once the impregnation was completed, the catalyst was dried and subsequently calcined at 480° C. for 1 hour.

Example 2

Catalyst 2 (Not According to the Invention)

A catalyst was made according to the procedure of Example 1 but differing in that 5% wt of $Na_2SiO_3$ (waterglass) was added to the mix of zeolite, silica powder and silica sol, dry basis. After extrusion, drying and calcining, the resulting extrudates had a sodium content of 1.22% wt, a water pore volume of 0.78 ml.g$^{-1}$ and a flat plate crushing strength of 104 N·m$^{-1}$.

After treating with the AHS solution, the resulting catalyst support had a sodium content of 0.43% wt, a water pore volume of 0.76 ml.g$^{A1}$ and a flat plate crushing strength of 163 N·m$^{-1}$.

Example 3

Catalyst 3

A support was made according to the procedure of Example 2 but differing in that after treating with the AHS solution, washing and drying, the extrudates were ion exchanged before being pore volume impregnated with the Pt/Sn solution. The ion exchange comprised immersing the extrudates in a 1 M $NH_4Cl$ solution at 90° C. for 1 hour, filtering out the extrudates, washing the extrudates with water and drying them at 120° C. The resulting support had a flat plate crushing strength of 163 N·m$^{-1}$.

Example 4

Catalyst 4

A support was made according to the procedure of Example 3 but differing in that the water contents of the mixture before extrusion was increased by 2% wt. The resulting extrudates had a sodium content of 1.18% wt, a water pore volume of 0.71 ml.g$^{-1}$ and a flat plate crushing strength of 136 N·cm$^{-1}$.

The extrudates were then subjected to the AHS treatment, washing, drying, ion exchange and drying according to Example 3. The support obtained had a sodium content of 0.22% wt before ion exchange. After the ion exchange, the support had a sodium content of 0.014% wt and a flat plate crushing strength of 170 N·cm$^{-1}$.

After metal impregnation, drying and calcining according to Example 1, the final catalyst had a flat plate crushing strength of 180 N·cm$^{-1}$.

Example 5

The support was prepared as described in Example 4 with the exception that the AHS treatment was carried out by treating the extrudates with the aqueous AHS solution and washing but replacing the last water wash step by washing with a 1 M $NH_4Cl$ solution. The washed extrudates were subsequently dried at 500° C. for 1 hour. The resulting support had a sodium content of 0.022% wt and a flat plate crushing strength of 168 N·cm$^{-1}$.

Example 6

The above catalysts were subjected to a catalytic test that mimics typical industrial application conditions for ethylbenzene dealkylation. The composition of the feed used is summarized in Table 1.

TABLE 1

| Composition of the Feed Used in the Activity Testing | | |
|---|---|---|
| Feed composition | | |
| EB | wt % | 13.68 |
| pX | wt % | 0.18 |
| oX | wt % | 18.12 |
| mX | wt % | 62.06 |
| toluene | wt % | 0.48 |
| benzene | wt % | 0.13 |
| $C_7$-$C_8$-naphthenes | wt % | 5.35 |
| $C_9^+$ aromatics | wt % | 0.00 |
| Total | wt % | 100.00 |
| $C_8$ aromatics | sum | 94.97 |
| EB in $C_8$ aromatics feed | wt % | 11.25 |
| pX in xylenes in feed | wt % | 0.22 |
| oX in xylenes in feed | wt % | 22.54 |
| mX in xylenes in feed | wt % | 77.23 |

The activity test is performed once the catalyst is in its reduced state, which is achieved by exposing the dried and calcined catalyst to atmospheric hydrogen (>99% purity) at 450° C. for 1 hour.

After reduction the reactor is pressurized without a cooling step, and the feed is introduced. This step contributes to enhanced catalyst aging, and therefore allows comparison of the catalytic performance at stable operation.

The catalytic datapoints are collected at a condition that exaggerates the potential negative operational effects. Therefore, the performance is measured not at the ideal industrial operating condition(s), but at those that allow a better differentiation of the various performance parameters used to evaluate catalysts in this application.

In the present case, a weight hourly space velocity of 4.6 h$^{-1}$, a hydrogen to feed ratio of 2.5 mol·mol$^{-1}$ and a total system pressure of 1.3 MPa was used. The temperature was varied between 360 and 410° C. to achieve the required conversion for easier comparison.

TABLE 2

Catalyst Properties

| | $T_{req.}$ for 75 wt % EBC °C. | Flat Plate Crushing Strength Support N · cm$^{-1}$ |
|---|---|---|
| Catalyst 1 (comparison) | 382 | 124 |
| Catalyst 2 (comparison) | 399 | 163 |
| Catalyst 3 | 362 | 163 |
| Catalyst 4 | 370 | 170 |
| Catalyst 5 | 353 | 168 |

$T_{req.}$ for 75 wt % EBC conversion stands for the temperature required to achieve 75 wt % EB conversion.

In all test runs, xylene isomerisation also occurred and in each case the content of p-xylene reached a minimum of 98% of its equilibrium value.

Table 2 shows the penalty on the activity of the catalyst by a high sodium content as exemplified by Catalyst 2. The highest gain in activity was obtained by Catalyst 5 in which ion exchange procedure was combined with the last washing step of the AHS treatment. An activity gain of almost 30° C. is attained.

Example 7 (Not According to the Invention)

A catalyst support was prepared following the preparation route described in Example 1, but with a ZSM-5 zeolite having a primary crystallite size in the range of a few cubic microns and a silica to alumina bulk molar ratio of 40. The extrudates had a sodium content of 0.13% wt before the AHS treatment.

The extrudates obtained were subjected to the AHS treatment as described in Example 5. The catalyst support obtained had a water pore volume of 0.69 ml·g$^{-1}$, a sodium content of 0.005% wt and a flat plate crush strength of 129 N·cm$^{-1}$, all before metal impregnation.

Example 8

A support was prepared by following the procedures of Example 5 but using the zeolite described in Example 7. The amount of Na$_2$SiO$_3$ (waterglass) added before extrusion gave a sodium content of the resulting extrudates of 1.20% wt.

After the combined AHS and ion exchange treatment, the catalyst support contained 0.07% wt sodium and had a water pore volume of 0.69 ml.g$^{-1}$ and a flat plate crushing strength of 170 N·cm$^{-1}$, all before metal impregnation.

Example 9

A support was prepared by following the procedures of Example 8 but adjusting the amount of Na$_2$SiO$_3$ (waterglass) added such as to obtain extrudates having a sodium content of 0.95% wt.

After the combined AHS and ion exchange treatment, the extrudates were dried. The support obtained contained 0.03% wt sodium and had a water pore volume of 0.68 ml·g$^{-1}$ and a flat plate crushing strength of 141 N·cm$^{-1}$, all before metal impregnation.

Example 10

A support was prepared by following the procedures of Example 9 but replacing the Na$_2$SiO$_3$ (waterglass) by NaOH solution such as to obtain extrudates having a similar sodium content. Upon analysis, it was found that the extrudates obtained had a sodium content of 0.98% wt.

After the combined AHS and ion exchange treatment, the extrudates were dried. The catalyst support obtained contained 0.03% wt sodium and had a water pore volume of 0.68 ml·g$^{-1}$ and a flat plate crushing strength of 151 N·cm$^{-1}$, all before metal impregnation.

That which is claimed is:

1. An ethylbenzene dealkylation catalyst, containing;
   a support obtainable by a process which comprises:
   a) mixing pentasil zeolite having a bulk silica to alumina molar ratio in the range of from 20 to 150 with water, a silica source and an alkali metal salt;
   b) extruding the mixture obtained in step (a);
   c) drying and calcining the extrudates obtained in step (b);
   d) treating the extrudates obtained in step (c) with an aqueous solution of fluorosilicate salt to provide fluorosilicate-treated extrudates;
   e) subjecting the fluorosilicate-treated extrudates obtained in step (d) to ion exchange with an aqueous ammonium containing solution to reduce the alkali metal content; and
   f) drying the extrudates obtained in step (e); and
   platinum in an amount in the range of from 0.001 to 0.1 wt % and tin in an amount in the range of from 0.01 to 0.5 wt %, each on the basis of total catalyst.

2. An ethylbenzene dealkylation catalyst as recited in claim 1, wherein the silica source is selected from the group consisting of powder form silica, silica sol, and mixtures of powder form silica and silica sol.

3. An ethylbenzene dealkylation catalyst as recited in claim 2, wherein silica source is a mixture of powder form silica and silica sol in a weight ratio of powder form silica-to-silica sol in the range of from 1:1 to 10:1, and wherein the powder form silica comprises small particulates having a mean particle size in the range of from 2 to 10 μm as measured by ASTM C690-1992.

4. An ethylbenzene dealkylation catalyst as recited in claim 3, wherein the catalyst support comprises silica in the range of from 30 to 80 wt % and zeolite in the range of from 20 to 70 wt %.

5. An ethylbenzene dealkylation catalyst as recited in claim 4, wherein the fluorosilicate salt is represented by the formula:

$$(A)_{2/b}SiF_6$$

wherein "A" is a metallic or non-non-metallic cation other than H$^+$ having the valence "b".

6. An ethylbenzene dealkylation catalyst as recited in claim 5, wherein the fluorosilicate salt is ammonium hexafluorosilicate (AHS).

7. An ethylbenzene dealkylation catalyst as recited in claim 6, wherein extrudates obtained in step (f) have a flat plate crush strength of at least 120 N·cm$^{-1}$.

8. An ethylbenzene dealkylation catalyst as recited in claim 7, wherein extrudates obtained in step (f) have a B.E.T. surface area in the range of from 150 to 250 m$^2$/g and a pore volume determined by mercury intrusion in the range of from 0.5 to 0.9 ml/g.

9. An ethylbenzene dealkylation catalyst as recited in claim 8, wherein the pentasil zeolite is ZSM-5 and is in the form of a powder comprising particles having diameters in the range of from 20 nm to 10 μm.

10. A process for dealkylation of ethylbenzene which process comprises contacting an ethylbenzene containing feedstock with the catalyst of claim 1.

11. A process for dealkylation of ethylbenzene which process comprises contacting an ethylbenzene containing feedstock with the catalyst of claim 2.

12. A process for dealkylation of ethylbenzene which process comprises contacting an ethylbenzene containing feedstock with the catalyst of claim 3.

13. A process for dealkylation of ethylbenzene which process comprises contacting an ethylbenzene containing feedstock with the catalyst of claim 4.

14. A process for dealkylation of ethylbenzene which process comprises contacting an ethylbenzene containing feedstock with a catalyst of claim 5.

15. A process for dealkylation of ethylbenzene which process comprises contacting an ethylbenzene containing feedstock with a catalyst of claim 6.

16. A process for dealkylation of ethylbenzene which process comprises contacting an ethylbenzene containing feedstock with a catalyst of claim 7.

17. A process for dealkylation of ethylbenzene which process comprises contacting an ethylbenzene containing feedstock with a catalyst of claim 8.

18. A process for dealkylation of ethylbenzene which process comprises contacting an ethylbenzene containing feedstock with a catalyst of claim 9.

* * * * *